United States Patent [19]

Cummins et al.

[11] Patent Number: 5,543,305

[45] Date of Patent: Aug. 6, 1996

[54] METHODS OF EXTRACTING DEOXYRIBONUCLEIC ACIDS WITHOUT USING A PROTEOLYTIC ENZYME

[75] Inventors: Thomas J. Cummins; Tobias D. Ekeze, both of Rochester, N.Y.

[73] Assignee: Johnson & Johnson Clinical Diagnostics, Inc., Rochester, N.Y.

[ * ] Notice: The term of this patent shall not extend beyond the expiration date of Pat. No. 5,231,015.

[21] Appl. No.: 471,806

[22] Filed: Jun. 6, 1995

Related U.S. Application Data

[60] Continuation of Ser. No. 10,249, Jan. 28, 1993, abandoned, which is a division of Ser. No. 423,071, Oct. 18, 1989, Pat. No. 5,231,015.

[51] Int. Cl.$^6$ .............................. C12P 19/34; C12Q 1/68; C07H 21/00
[52] U.S. Cl. ........................ 435/91.1; 435/6; 435/91.2; 435/810; 436/501; 536/22.1; 536/23.1; 536/24.1; 536/24.3; 536/24.31; 536/24.32; 536/24.33; 536/25.4; 935/7; 935/77; 935/78
[58] Field of Search .................................. 435/5, 6, 91.1, 435/91.2, 810; 436/501; 536/22.1, 23.1, 24.1, 24.3–24.33, 25.4; 935/7, 77, 78

[56] References Cited

U.S. PATENT DOCUMENTS

| | | | |
|---|---|---|---|
| 4,750,982 | 6/1988 | Tomblin et al. | 204/299 |
| 4,900,677 | 2/1990 | Hewitt | 435/259 |
| 5,231,015 | 7/1993 | Cummins et al. | 435/91 |
| 5,334,499 | 8/1994 | Burdick et al. | 435/6 |

FOREIGN PATENT DOCUMENTS

| | | |
|---|---|---|
| 237362 | 5/1983 | European Pat. Off. . |

OTHER PUBLICATIONS

Signer et al, *Nucleic Acids Res.*, 16(15), p. 7738 (1988).
Higuchi, *Amplifications*, May, 1989, pp. 1 and 3.
Kogan et al, *N. Eng. J. Med.*, 317(6), pp. 985–990 (1987).
Saiki et al, *Nature*, 324(6093), pp. 163–166 (1986).
Saiki et al, *Bio/Technology*, 3, pp. 1008–1012 (1985).
Bell et al, *Proc. Natl. Acad. Sci. USA*, 78(9), pp. 5759–5783 (1981).
Adler et al, Jun. 8, 1989, Abstract entitled "Detection of HIV–I DNA is Peripheral Blood by Polymerase Chain Reaction (PCR) and Non–Radioactive Oligonucleotide Probes".
Owen et al, *Nucleic Acid Research:*, 15(8), p. 3631, 1987.
Longmire et al, *Nucleic Acids Research*, 15(2), p. 859, 1987.
Buffone et al, *Clin. CHem.*, 31(1), pp. 164–165 (1985).
Kolodner et al, *Biochim. Biophysi Acta*, 402, pp. 372–390, 1975.
Beji et al, *Anal. Biochem.*, 162, pp. 18–23 (1987).
Blin et al, *Nucl. Acids Research.*, 3(9), ppl 2303–2308, 1976.
Hillenbrand et al. (1982) Nucleic Acids Res., vol. 10, No. 3, pp. 838–853.
Hutchison et al, Cell, vol. 43, pp. 471–482 (1985).
*Webster'S II, New Riverside Dictionary*(Ed. A. Soukhanov et al., Houghton Mifften Co., Boston, MA., 1984), p. 948.

*Primary Examiner*—W. Gary Jones
*Assistant Examiner*—Ardin H. Marschel

[57] ABSTRACT

This invention provides a rapid and highly effective method for extracting nucleic acids from cells or virions without the use of proteolytic enzymes. Extraction is accomplished within a few minutes using a lysing composition comprising a buffer, a source of a DNA polymerase cofactor, a stabilizer and at least one nonionic surfactant which will release nucleic acids from cytoplasmic and nuclear membranes of cells or virions. The resulting mixture is heated to boiling for up to fifteen minutes, and the nucleic acids are recovered for amplification using polymerase chain reaction. No proteolytic enzyme is used in the extraction process.

15 Claims, No Drawings

METHODS OF EXTRACTING DEOXYRIBONUCLEIC ACIDS WITHOUT USING A PROTEOLYTIC ENZYME

This is a continuation of application Ser. No. 08/010,249, filed Jan. 28, 1993, now abandoned, which is a divisional of application Ser. No. 423,071, filed Oct. 18, 1989, now U.S. Pat. No. 5,231,015.

FIELD OF THE INVENTION

The present invention relates to a rapid and effective method for extracting nucleic acids from cellular or vital materials. It also relates to a method for amplifying or detecting the extracted nucleic acids. Thus, the methods can be used for diagnostic purposes.

BACKGROUND OF THE INVENTION

Within the field of biological diagnostics, research and analytical procedures require the investigation of nucleic acids from biological specimens, such as whole blood or fractions thereof. Such in vitro procedures require as a first step, the isolation of the nucleic acids. For example, relatively pure samples of genomic DNA are required in order to perform tests for genetic diseases, and recombinant technology requires isolation of both the vector DNA and the DNA to be cloned. In the detection of infectious agents, such as bacteria and vitally infected cells, DNA diagnostic procedures generally require cell lysis followed by detection of the released DNA.

Generally, DNA does not exist as a free molecule in a cell, but instead exists as a complex association of DNA, RNA and proteins. This is a consequence of the role of DNA as the carrier of genetic information, and its involvement with RNA and various proteins in that function.

Because of this complex association of DNA with other materials in a specimen, effective DNA extraction requires that: the DNA be released through disrupted cell walls and membranes, DNA-protein complexes be dissociated by denaturation or proteolysis, and DNA be separated from other macromolecules. Various means are used in the art to accomplish one or more of these results. Cell lysis can be accomplished, for example, by freeze-thawing, ultrasonic means, shearing and other mechanical techniques, or by treatment with enzymes, surfactants or chelating agents. Proteases and other hydrolyzing agents can be used to dissociate DNA from proteins. Residual proteins and other macromolecules can be extracted using various solvents, such as phenol or other alcohols.

Some DNA isolation techniques are described in, for example, EP-A-0 145 356 (published Jun. 19, 1985), EP-A-0 240 191 (published Oct. 7, 1987), and EP-A-0 245 945 (published Nov. 19, 1987), all of which use an alcohol and an enzymatic protein decomposer in certain sequences of steps. Generally, these procedures are directed to the extraction of vital DNA and involve a number of complicated steps which must be carried out with precision in order to obtain all available DNA. Thus, many of the known processes are labor intensive, require the use of undesirable solvents and are not readily automated.

Isolation or extraction of the nucleic acid of interest is necessary to take advantage of recent developments for amplification and detection of nucleic acids using polymerase chain reactions. U.S. Pat. No. 4,683,195 (issued Jul. 28, 1987 to Mullis et al) and U.S. Pat. No. 4,683,202 (issued to Mullis the same day) describe useful amplification and detection procedures for nucleic acids found in various biological specimens using a polymerase. Standard nucleic acid extraction techniques are mentioned by reference to Manjarls et al, *Molecular Cloning: A Laboratory Manual* (New York: Cold Spring Harbor Laboratory, 1982), pp. 280–281. This reference is directed to a standard extraction procedure involving the use of a protease to lyse cells and phenol/chloroform extraction, the entire procedure generally taking many hours to perform and involves the use of hazardous organic solvents. It is also used to extract DNA: from hamster ovary cells by Nunberg et al, *Proc.Natl.Acad.Sci.USA*, 75(11), pp. 5553–5556 (1978), from the buffy coat of whole blood specimens by Saiki et al, *Bio/Technology*, 3, pp. 1008–1012 (1985), and from whole blood by Bell et al, *Proc.Natl.Acad.Sci.USA*, 78(9), pp. 5759–5763 (1981).

For diagnostic testing to be commercially feasible, it also must be economically competitive. This means that every aspect of the procedure must be simple, easy to use and automated to some extent. Extraction of the DNA from a specimen is one aspect that requires careful development in order to obtain maximum amounts of DNA from the specimen as well as economic advantages. Moreover, in situations where a diagnostic result is needed quickly the extraction procedure should be rapid.

Thus, there has been considerable activity in developing improved DNA extraction procedures which avoid the tedious and time-consuming steps noted above and the use of organic solvents. Thus, Kogan et al, *N.Eng.J.Med.*, 317(16), pp. 985–990 (1987) describe the extraction of DNA to detect genetic disorders by boiling cells which have been removed from whole blood by centrifugation. The extracted DNA is then subjected to amplification.

Similarly, Saiki et al, *Nature*, 324, pp. 163–166 (1986) describe boiling buffered buffy coat (which includes peripheral blood mononuclear cells and granulocytes) of whole blood to amplify β-globin DNA. Similar work is shown in EP-A-0 237 362 for detection of sickle cell and HLA DNA. In some cases, the cells of the buffy coat are overlaid with mineral oil prior to the heating step.

While these procedures avoid the tedious phenol/chloroform extraction described above, and appear to be rapid (done in a few minutes), they are largely useful only for extraction of DNA present in large quantities in a whole blood sample, such as HLA or β-globin DNA. Where the DNA of interest is present in very small quantities, such as in the case of the presence of many infectious agents (such as viruses), further improvements in extraction from whole blood, or a buffy coat fraction, are needed for sensitive detection. Moreover, there are many interferents to polymerase activity which also need to be removed from whole blood prior to amplification.

A recent innovation is described in U.S. patent application Ser. No. 406,222 (filed Sep. 12, 1989 by Burdick and Ekeze) which is a CIP of U.S. patent application Ser. No. 339,437 (filed Apr. 17, 1989 by the same persons), now abandoned. These applications are directed to the boiling of whole blood or peripheral blood mononuclear cell fraction (PBMC) thereof to extract DNA. While it has been found that such procedures do extract DNA from specimens, further improvements in sensitivity are needed.

Still another recent advance in the art is described in U.S. patent application Ser. No. 178,202 (filed Apr. 6, 1988 by Higuchi) whereby the defects of the tedious phenol/chloroform procedure are avoided, and which allows extraction of DNA for polymerase chain reaction. It involves the use of a composition containing a nonionic lysing detergent and a proteolytic enzyme, such as proteinase K. One of the principle advantages of this method is the shortening of the time for DNA extraction to less than two hours. This procedure is also described by Higuchi in *Amplifications, A Forum for PCR Users, Issue* 2, pp. 1 and 3, May, 1989.

While this improvement is welcome in the art, there is a continuing need to simplify DNA extraction procedures even further, especially where the DNA is present in very small concentrations in the specimen. In particular, there is a need for a rapid and effective method of extracting nucleic acids which do not require one or two hours to perform. Thus, a considerably shortened and simplified sample preparation procedure is needed for high volume diagnostic situations.

SUMMARY OF THE INVENTION

The problems encountered with extraction procedures of the prior art are overcome with a method for the rapid extraction of a nucleic acid from cells or virions, the method consisting essentially of:

A. mixing a sample of cells or virions containing one or more nucleic acids with a lysing composition comprising, in the absence of proteolytic enzymes, (1) an organic buffer which maintains the composition at a pH of from about 4 to about 10, (2) a source of a catalytic amount of a cofactor for DNA polymerase activity, (3) a stabilizer, (4) at least one compatible nonionic surfactant present in an amount sufficient to release nucleic acids from cytoplasmic and nuclear membranes of the cells or virions, B. heating the resulting mixture at or near the boiling point of water for from about five to about fifteen minutes, and C. recovering the nucleic acids from the heated mixture.

This invention also provides a method for amplifying a nucleic acid using polymerase chain reaction, the method comprising:

I. an extraction procedure consisting essentially of:

(A) mixing a sample of cells or virions containing one or more nucleic acids with a lysing composition comprising, in the absence of proteolytic enzymes, (1) an organic buffer which maintains the composition at a pH of from about 4 to about 10, (2) a source of a catalytic amount of a cofactor for DNA polymerase activity, (3) a stabilizer, (4) at least one compatible nonionic surfactant present in an amount sufficient to release nucleic acids from cytoplasmic and nuclear membranes of the cells or virions, B. heating the resulting mixture at or near the boiling point of water for from about five to about fifteen minutes, and C. recovering the nucleic acids from the heated mixture, and II. amplifying the recovered nucleic acid using a polymerase chain reaction.

The extraction method of this invention is rapid and effective to extract nucleic acids from cells or virions in a variety of patient specimens. The method can be carried out in as little as fifteen minutes, thereby avoiding the tedious procedures of the art. No organic solvents are needed, and there are few steps to the procedure so it susceptible to automation, for example in a contained vessel of some type. An operator can readily use the method of this invention and obtain a diagnostic result quickly.

The use of expensive proteolytic enzymes, such as proteinase K, is avoided with this invention. Unexpectedly, the procedure is carried out within a few minutes, unlike the one to two hour protocol of U.S. patent application Ser. No. 178,202 (noted above). Without the presence of the proteolytic enzymes, there is no need for time-consuming deactivation steps, or a need to avoid reagents which prematurely deactivate the enzymes.

These advantages are achieved by the use of a specific extraction composition which includes the reagents normally used in polymerase chain reaction amplification. In fact, the reagents are similar to those used in U.S. patent application Ser. No. 178,202 (noted above), but unexpectedly without the proteolytic enzyme. The composition is readily mixed with the patient specimen, boiled for a few minutes and then the released nucleic acids are isolated in a suitable manner. The diluent compositions described in U.S. patent application Ser. No. 406,222 (noted above) are also avoided with this invention. As noted above, following extraction, the reaction mixture is ready for amplification.

DETAILED DESCRIPTION OF THE INVENTION

The present invention is directed to the extraction or amplification of one or more nucleic acids from any specimen containing whole cells, virions or components thereof from any source (human, animal or plant tissue or fluids). Preferably, whole blood or a component thereof is the source of the nucleic acids. While the primary purpose of the invention is diagnostic, extracted nucleic acids can also be used in various research and medical studies, for cloning DNA or messenger RNA or for sequencing genomic DNA. Other uses for extracted nucleic acids would be readily apparent to one skilled in the art.

Nucleic acids can be genomic DNA or that generated in cells or fluids by infectious agents such as bacteria, viruses or yeasts. The samples containing nucleic acids can be fresh patient samples, fresh or frozen cell pellets, or provided in any other suitable form. Where the specimen treated is whole blood, generally the nucleic acid extracted is genomic DNA. However, this invention is particularly useful for extracting and detecting DNA from cells invaded by infectious agents (most likely viruses such as Herpes, Cytomegalovirus, Epstein-Bart virus, hepatitis, rubella, and retroviruses such as HIV-I, HIV-II and HTLV-I). Preferably, Cytomegalovirus, Epstein-Bart viral and HIV-I viral DNA are extracted and detected with the present invention, with the extraction and detection of HIV-I viral DNA being of most interest.

In a preferred embodiment, the extracted nucleic acid is amplified and detected using polymerase chain reaction (described in more detail below).

One component of whole blood which can be a source of nucleic acids is the peripheral blood mononuclear cell fraction (PBMC). This is obtained from whole blood by centrifugation onto a cushion of Ficoll-Paque™ (Pharmacia Inc., Piscataway, N.J.), using standard procedures. It is believed to be composed of monocytes and lymphocytes.

The sample containing cells or virions is mixed with a lysing composition at a temperature which facilitates lysing the cells or virus particles. Generally, the temperature is from about 15° to about 30° C., with room temperature being most usual.

It is critical that no proteolytic enzymes be used in the method of this invention. Such enzymes are generally defined in U.S. patent application Ser. No. 178,202 (noted above) as any enzyme or enzyme preparation which catalyzes the hydrolytic degradation of proteins.

The lysing composition includes one or more organic buffers which maintain the pH at from about 4 to about 10, and preferably at from about 7 to about 9. Useful buffers include, but are not limited to 3-(N-morpholino)propanesulfonic acid, 3-(N-morpholino)ethanesulfonic acid, tricine, glycine, tris(hydroxymethyl)aminomethane and others readily apparent to one skilled in the art. Preferably, tris(hydroxymethyl)aminomethane is used. The amount of buffer used is dependent upon the $pK_a$ and is that sufficient to maintain the desired pH. Generally, it is present in a molar concentration of from about 1 to about 100 mmolar.

A source of a cofactor for a DNA polymerase is also included in the composition. Useful cofactors are generally metal ions, such as magnesium and manganese ions. They can be supplied as free ions, or as salts, such as magnesium chloride, magnesium acetate, magnesium bromide, magnesium sulfate, manganese chloride, manganese bromide or others readily apparent to one skilled in the art. The amount of cofactor included is variable with the other reagents used in amplification, such as the polymerase, primers and other considerations apparent to one skilled in the art, as long as there is a catalytic amount which is that amount needed to effectively promote DNA polymerase activity. Generally, the amount is at least about 0.5, and preferably from about 1 to about 20, mmolar. Magnesium ions are preferred in the form of magnesium chloride.

A stabilizing material is also included in the composition. This material could also be considered a binder material. It can be one or more synthetic or naturally occurring water-soluble or water-dispersable high molecular weight material, such as proteins which will not complex with the nucleic acids being extracted, gelatin or a derivative thereof, cellulose or a derivative thereof, polyvinyl alcohol, polyethylene glycol and others which would be readily apparent to one skilled in the art. The stabilizer is generally present in an amount of from about 0.1 to about 10 mg/ml of composition.

The lysing composition includes one or more compatible nonionic surfactants present in an amount sufficient to release nucleic acids from cytoplasmic and nuclear membranes of the cells or virus particles in the test specimen. By "compatible" is meant that the surfactant does not adversely affect the nucleic acids being extracted or any of the other materials used in the lysing composition.

There are a variety of classes of nonionic surfactants which can be used in the composition including, but not limited to, polyoxyethylenesorbitan derivatives, polyoxyethylene ethers, polyglycol ethers, perfluoroalkylpolyoxyethylenes, fluorinated alkyl alkoxylates and fluorinated alkyl ester compounds. Other useful classes of surfactants and examples of each class would be readily apparent to one skilled in the art, especially after consulting the standard reference for surfactants, *McCutcheon's Emulsifiers and Detergents*, 1986 North American Edition, McCutcheon Division Publishing Co., Glen Rock, N.J.

Representative polyoxyethylenesorbitan derivatives include, but are not limited to, polyoxyethylene (20) sorbitan monolaurate (sold as Tween™ 20), polyoxyethylene (4) sorbitan monolaurate (sold as Tween™ 21), polyoxyethylene (20) sorbitan monopalmitate <sold as Tween™ 40) and polyoxyethylene (20) sorbitan monostearate (sold as Tween™ 60) and other sold under the Tween™ mark by ICI Americas, Inc.

Representative polyglycol ethers include, but are not limited to, those sold by Union Carbide as Tergitol™ nonionic surfactants (such as Tergitol™ NPX and Tergitol™ NP-7).

Representative surfactants which belong to the fluorinated classes noted above include, but are not limited to, the Zonyl™ surfactants (from DuPont) such as Zony™ FSN and Zonyl™ FSN-100, the Fluorad™ surfactants available from 3M Company, such as Fluorad™ FC-170-C, Fluorad™ FC-170, Fluorad™ FC-430, Fluorad™ FC-431 and Fluorad™ FC-740.

Useful polyoxyethylene ethers include, but are not limited to, those sold under as Triton™ surfactants by Rohm and Haas, such as octylphenoxy polyethoxy ethanol (sold as Triton™ X-100 or Triton™ X-102 or as Nonidet™ NP-40 by Sigma Chemical), nonylphenoxy polyethoxy ethanol (sold as Triton™-N), or those sold as Brij™ surfactants by ICI Americas, Inc., such as polyoxyethylene (23) lauryl ether (sold as Brij™ 35) or polyoxyethylene (2) cetyl ether (sold as Brij™ 52).

Generally, at least two nonionic surfactants are used, one each from two different classes of surfactants. Preferred classes are the polyoxyethylene ethers and polyoxyethylenesorbitan derivative. Thus, a preferred embodiment includes a surfactant from each of these two classes, such as Triton™ X-100 or Nonidet™ NP-40 with Tween™ 20.

The amount of nonionic surfactant in the lysing composition is variable depending upon the amount of cellular or vital material believed to be present. It is dependent largely upon how sensitive the amplification procedure is to detect extracted nucleic acids. The more nucleic acids to be released, the greater the amount of surfactant preferably present. Generally, it is present in an amount of at least about 0.1, and preferably from about 0.1 to about 5, percent (based on total composition weight). Where a multiplicity of surfactants is present, the amount of surfactant can be apportioned to individual surfactants as desired. Preferably, where there is a surfactant from more than one class, the surfactants are present in equal amounts.

Optionally, but preferably, the lysing composition contains a salt in an amount of from about 1 to about 150 mmolar, and more preferably from about 50 to about 100 mmolar. Such salts are those which are ionized in aqueous solution to a high degree, and include monovalent salts such as sodium chloride, potassium chloride and others known to one skilled in the art. Alkali metal salts are preferred, and potassium chloride is most preferred. Alternatively, a compound sufficiently ionized at the pH of the lysing composition, but which may not be completely ionized under all conditions, may be used. Examples of such compounds include buffers, such as tricine, glycine, sodium glycinate, sodium tricine, 3-(N-morpholino)propanesulfonic acid, sodium salt and others known to one skilled in the art. A mixture of compounds may be used. Moreover, the salt may be supplied by one or more of the listed components of the lysing composition rather than as an additional compound.

After the test sample and lysing composition are mixed for a sufficient time (usually less than about 10 minutes), a critical step in the extraction method of this invention is to subject the mixture to heat at or near the boiling point of water for a sufficient time to break down proteins and lyse all cells in the sample. The temperature for this step would vary depending upon atmospheric pressure, the time of boiling and other environmental factors. Generally, at sea level, the temperature for heating would be at or near 100° C., but could be as low as 80° C. and as high as 120° C.

The time of maintaining the sample at the temperature noted above is that needed to denature the proteins and lyse the cells and virions in the sample to release the nucleic acids. This can be readily determined by taking portions of the sample during the heating step and determining whether whole proteins remain. The time will also vary with the temperature used, that is, the lower the temperature, the longer the period of heating time. Generally, the sample is heated at the desired temperature for at least about five minutes and up to about fifteen minutes, and preferably from about eight to about twelve minutes, with about ten minutes being optimum.

Heating can be carried out in any suitable vessel which is sufficient in size to hold the sample and which can withstand the heating procedure. For example, it can be carried out in flasks, test tubes, centrifuge tubes, capillary tubes, beakers, cuvettes and other standard laboratory equipment. Preferably, it is carried out in a self-contained reaction vessel which is designed for various procedures including heating and chemical reactions. Many such vessels are known in the art. A preferred self-contained vessel is described in copending U.S. patent application Ser. No. 339,923 (filed Apr. 14, 1989 by Schnipelsky et al).

After heating, the released nucleic acid (generally, DNA) is recovered in a suitable manner. Cellular matter and any coagulated debris are separated from the fluid containing soluble DNA molecules in any suitable manner, including filtration, centrifugation, decanting or siphoning. Filtration can be carried out using standard filtration equipment, or various devices having filtration membranes. Particularly useful separation means are microporous filter membranes such as the polyamide membranes marketed by Pall Corp. (for example as Loprodyne™ or Biodyne™ membranes). They can be used uncoated or precoated with surfactants or other materials which facilitate the analytical procedures.

The membranes can be used as a separate substrate with suitable containers for carrying out other steps of the assay. Preferably, however, it is mounted as part of a test device. Various test devices are known in the art including those described in U.S. Pat. No. 3,825,410 (issued Jul. 23, 1974 to Bagshawe), U.S. Pat. No. 3,888,629 (issued Jun. 10, 1975 to Bagshawe), U.S. Pat. No. 3,970,429 (issued Jul. 20, 1976 to Updike) and U.S. Pat. No. 4,446,232 (issued May 1, 1984 to Liotta). Particularly useful devices are described in EP-A-0 308 231 (published Mar. 22, 1989).

The method of this invention includes the steps outlined above, and no others are generally needed. However, where a whole blood specimen is used, it may be desirable to remove the red blood cells in a suitable manner. Other optional centrifugation steps may be useful in the method to remove potential interferents or cellular debris before either the mixing or heating step.

In a preferred embodiment of this invention for the rapid extraction of HIV-I DNA from a patient specimen, the method consists essentially of:

A. mixing a patient specimen believed to contain HIV-I infected cells with a lysing composition comprising, in the absence of proteolytic enzymes,
  (1) an organic buffer which maintains the composition at a pH of from about 4 to about 10,
  (2) a source of at least about 0.5 mmolar of magnesium ion,
  (3) a stabilizer,
  (4) at least one compatible nonionic surfactant present in an amount sufficient to release HIV-I DNA from cytoplasmic and nuclear membranes of the cells, B. heating the resulting mixture at or near the boiling point of water for from about five to about fifteen minutes, and
C. recovering HIV-I DNA from the heated mixture.

More specifically, a method for the rapid extraction of a nucleic acid from cells or virions consists essentially of:
A. mixing a sample of cells or virions containing one or more nucleic acids with a lysing composition comprising, in the absence of proteolytic enzymes,
  (1) tris(hydroxymethyl)aminomethane to maintain the composition at a pH of from about 7 to about 9,
  (2) from about 1 to about 150 mmolar potassium chloride,
  (3) from about 0.5 to about 20 mmolar magnesium ion,
  (4) from about 0.1 to about 10 mg of gelatin per ml of composition,
  (5) from about 0.1 to about 5 weight percent of a polyoxyethylenesorbitan derivative nonionic surfactant, based on total composition weight,
  (6) from about 0.1 to about 5 weight percent of a polyoxyethylene ether nonionic surfactant, based on total composition weight, B. heating the resulting mixture at or near the boiling point of water for from about eight to about twelve minutes, and
C. recovering the nucleic acids from the heated mixture.

As used herein in referring to primers, probes or nucleic acid fragments to be detected, the term "oligonucleotide" refers to a molecule comprised of two or more deoxyribonucleotides or ribonucleotides, and preferably more than three. The exact size is not critical but depends upon many factors including the ultimate use or function of the oligonucleotide. The oligonucleotide may be derived synthetically or by cloning.

The term "primer" refers to an oligonucleotide, whether naturally occurring or synthetically produced, which is capable of acting as a point of initiation of synthesis when placed under conditions in which synthesis of a primer extension product complementary to a nucleic acid strand is induced. Such conditions include the presence of nucleotides (such as the four standard deoxyribonucleoside triphosphates) and an agent for polymerization such as a DNA polymerase, and suitable temperature and pH.

In the practice of this invention, primers, probes and fragments are substantially complementary to a specific nucleic acid sequence of the targeted nucleic acid extracted from whole blood or PBMC fraction. By "substantially complementary" is meant that there are a sufficient number of bases on complementary materials that match so that hybridization will occur. It does not mean, however, that every base pair will match.

In the amplification and detection methods of this invention, useful primers can be obtained from a number of sources or prepared using known techniques and equipment, including for example, an ABI DNA Synthesizer (available from Applied Biosystems) or a Biosearch 8600 Series or 8800 Series Synthesizer (available from Milligen-Biosearch, Inc.) and known methods for their use. Naturally occurring primers isolated from biological sources are also useful (such as restriction endonuclease digests).

In some embodiments, at least one of the primers (or sets thereof) used in the detection method is labeled with a specific binding ligand. The term "labeled" refers to the fact that the ligand is attached to this primer in a manner such that it will not readily be detached. The specific binding ligand can be biotin or a derivative thereof, avidin, streptavidin or a derivative thereof, a lectin, a sugar, a protein, a hapten, a drug, or an immunological species, such as an antibody or an antigenic material. Further details about such primers and their use are provided in copending U.S. patent application Ser. No. 273,779 (filed Nov. 21, 1988 by Burdick et al), incorporated herein by reference, now abandoned.

The present invention is useful for amplification or detection of a targeted nucleic acid having two complementary strands. Most nucleic acid sequences of interest already are double-stranded, such as those found in DNA. However, single-stranded nucleic acid sequences, such as mRNA, can be similarly amplified and detected.

A specific nucleic acid sequence is produced using the nucleic acid containing that sequence as a template. If the nucleic acid contains two strands, it is necessary to separate the strands (called denaturation), either as a separate step or simultaneously with the formation of primer extension products. Denaturing can be accomplished using any suitable physical, chemical or enzymatic means as described in the art. Heating to a suitable temperature is a preferred means.

Once the separated strands are available for use, synthesis of additional nucleic acid strands can be carried out using two or more primers (labeled or unlabeled) in a buffered aqueous solution generally at a pH of from about 7 to about 9. Preferably, a molar excess of the two primers is added to the buffered solution, and specific amounts are taught in the art (for example, U.S. Pat. No. 4,683,202). The deoxyribonucleoside triphosphates dATP, dCTP, dGTP and dTTP are also added to the synthesis mixture in adequate amounts and the resulting solution is heated to about 90°–100° C. for up to 10 minutes, and preferably from about 1 to about 4 minutes. Enzyme cofactors, such as magnesium or manganese ions, are also preferably present in molar excess to the triphosphates. After this heating, the solution is preferably cooled to room temperature, and an appropriate agent for inducing (or catalyzing) the formation of primer extension products is introduced. This inducing agent is generally known in the art as a polymerization agent. Reaction to form these products is carried out under known conditions (generally from room temperature to that temperature at which polymerization no longer occurs).

The polymerization agent may be any compound, or combination of reagents, which will function to accomplish the synthesis of primer extension products, including enzymes (for example, *E. coli* DNA polymerase I, T4 DNA polymerase, Klenow polymerase, reverse transcriptase and others known in the art). Particularly useful enzymes are thermally stable enzymes, cloned or naturally occurring, such as those obtained from various Thermus and Methanothermus bacterial species. Other polymerization agents are described in U.S. Pat. No. 4,683,202, incorporated herein by reference.

Preferred thermal-stable enzymes are native DNA polymerases derived from *Thermus aquaticus,* or synthetically produced from a gene cloned from a genome of the microorganism, as described in EP-A-0 258 017 (published March 2, 1988). Those polymerases generally have a molecular weight of about 86,000–90,000 daltons. Other useful enzymes are described by Rossi et al, *Syst. Appl. Microbiol.* 7(2–3), pp. 337–341, 1986. Some useful polymerases are commercially available. Generally, the synthesis of extension products will be initiated at the 3' end of each primer and proceed in the 5' to 3' direction along the template until synthesis is terminated. Some polymerization agents (for example, reverse transcriptase) may proceed in the 3' to 5' direction along the template.

The newly formed primer extension products comprising the newly synthesized strands and their respective primers form double-stranded molecules with the initial target strands which are used in the succeeding steps of the method. These strands are then separated by denaturation as described above to provide single-stranded molecules, onto which new nucleic acids are synthesized as described above. Additional reagents may be needed to keep the amplification procedure going, after which most of the extension products will consist of the specific nucleic acid sequence bounded by the two primers (that is, complementary products).

The steps of strand separation and extension product synthesis can be repeated as often as needed to produce the desired quantity of the specific nucleic acid needed for the use, for example detection. Generally, the sequence of steps is repeated at least once, and preferably at least 10 to 50 times.

When it is desired to amplify more than one targeted extracted nucleic acid, the appropriate number of sets of primers are used in the general procedure described above.

Various detection procedures can be used to determine the presence of the detectable hybrid including Southern blot, gel electrophoresis, staining and others known in the art.

At any point in the method of this invention after the generation of at least one primer extension product, that product can be hybridized with a detectably labeled probe (described below).

Generally, once a desired amount of the nucleic acid sequence of interest has been generated and the primer extension products are separated for a last time, the first primer extension product is contacted with an oligonucleotide probe which is labeled for detection and is complementary thereto to form a product. The probe comprises an oligonucleotide which is complementary with the targeted nucleic acid sequence. The probes can be of any suitable length of nucleic acids, but preferably they have from about 15 to about 40 nucleic acids. They are labeled (commonly at the 5' end) with any suitable detectable material which will not interfere with the complexation of the specific binding ligand and its receptor. Procedures for attaching labels and preparing probes is well known in the art, for example, as described by Agrawal et al, *Nucleic Acid Res.,* 14, pp. 6227–45 (1986), and in the references noted above for attaching a specific binding ligand to a primer. Useful labels include radioisotopes, electron-dense reagents, chromogens, fluorogens, phosphorescent moieties, ferritin and other magnetic particles, chemiluminescent moieties and enzymes (which are preferred). Useful enzymes include, glucose oxidase, peroxidase, uricase, alkaline phosphatase and others known in the art. Substrates and dye forming compositions for such enzymes are well known.

In a particularly preferred embodiment, the label is peroxidase, and at some point in the assay, hydrogen peroxide and suitable dye-forming compositions are added to provide a detectable dye. For example, useful dye-providing reagents include tetramethylbenzidine and derivatives thereof, and leuco dyes, such as triarylimidazole leuco dyes (as described in U.S. Pat. No. 4,089,747, issued May 16, 1978 to Bruschi), or other compounds which react to provide a dye in the presence of peroxidase and hydrogen peroxide. Particularly useful dye-providing compositions are described in WO-A-0 88/02806 and 88/02807 (both filed Aug. 16, 1988) and U.S. patent application Ser. No. 136,166 (filed Dec. 18, 1987, now U.S. Pat. No. 5,024,935 by McClune et al).

Detection of the presence of the probe which is in the complementary product can be achieved using suitable and known detection equipment and procedures. Certain probes may be visible to the eye without the use of detection equipment.

In order for the probe in the complementary product to be detected, it is often important for the complementary product to be separated from the other materials in the reaction medium. This can be done by suitable insolubilization means, such as by using a primer or probe which is attached or capable of becoming attached to a solid material at some point in the method. The resulting insolubilized complexed product can be separated from uncomplexed materials by filtration, centrifugation or other suitable separation techniques.

Particularly useful separation means are microporous filter membranes such as the polyamide membranes marketed by Pall Corp. (described above). The membranes can be used as a separate substrate with suitable containers for carrying out other steps of the assay. Preferably, however, they are mounted as part of a test device, as described above.

The method described herein can be used to provide the detection or characterization of specific nucleic acid sequences associated with infectious diseases, genetic disorders or cellular disorders such as cancers found in biological specimens. It may also be used in forensic investigations, DNA typing and tissue typing. For purposes of this invention, genetic diseases include specific deletions or mutations in human genomic DNA from any organism, such as sickle cell anemia, cystic fibrosis, α-thalassemia, β-thalessemia and others readily apparent to one skilled in the art. Various infectious diseases can be diagnosed by the presence in the cells of small quantities of specific DNA sequences characteristic of the organism, whether it be a yeast, bacterium or virus. Such bacteria which can be detected include, but are not limited to, Salmonella, Chlamydia, Gonorrhea, Shigella and Listeria. Viruses which are detectable include, but are not limited to, herpes, Cytomegalovirus, Epstein-Barr virus, hepatitis and retroviruses such as HTLV-I and HIV-I. Protozoan parasites, yeasts and molds are also detectable. Other detectable species would be readily apparent to one skilled in the art.

The following examples are included to illustrate the practice of this invention, and are not meant to be limiting in any way.

The materials used in the examples were as follows:

The "running buffer" (pH 8) used for electrophoresis was composed of tris(hydroxymethyl)aminomethane (89 mmolar), boric acid (89 mmolar) and ethylenediaminetetraacetic acid (2 mmolar).

Hanks balanced salt solution was obtained from Sigma Chemical Co.

The dye used to quantitate DNA was 2-[2-( 4-hydroxyphenyl)-6-benzimidazole]-6-(1-methyl- 4-piperazyl)benzimidazole, trihydrochloride obtained from Calbiochem.

Leucoprep™ tubes were obtained from Becton Dickerson Labware (Lincoln Park, N.J.).

Cells were counted using an Olympus BH-2 microscope from Spectra Services (Rochester, N.Y.).

The DNA was quantitated as follows: after centrifugation, the supernatant (5 µl) containing the DNA was added to a buffer solution (2 ml) containing the imidazole dye identified above (final concentration of 0.1 g/ml). The buffer solution contained tris(hydroxymethyl)aminomethane (10 mmolar) ethylenediaminetetraacetic acid (1 mmolar) and sodium chloride (0.1 molar) with the pH adjusted to 7.4 using hydrochloric acid. The fluorescence was measured in a TK0 100 minifluorometer (Hoefer Scientific, San Francisco) and compared to a standard curve to quantitate the DNA.

The primers used in the amplification had the following sequences:
Primer 1: 5'-UGCTATGTCAGTTCCCCTTGGTCTTC-3'
Primer 2: 5'-UAGTGGGGGGACATCAAGCAGCCATGCAAA-3'
Primer 3: 5'-AGCAGCAGGAAGCAGTATGG-3' and
Primer 4: 5'-UCCAGACTGTGAGTTGCAACAG-3'. Primers 1 and 2 amplify a nucleic acid sequence in the gag region of HIV-I DNA while Primers 3 and 4 amplify a nucleic acid sequence in the env region of HIV-I DNA.

Agarose gel, 3% SuSieve™ and 1% Seakem™ were obtained from FMA BioProducts (Rockland, Me.).

The Control lysis composition (like that of U.S. patent application Ser. No. 178,202, noted above) was prepared as follows: Tris(hydroxymethyl)aminomethane hydrochloride buffer (10 mmolar, pH 8.3), potassium chloride (50 mmolar), magnesium chloride (2.5 mmolar), gelatin (0.1 µg/ml), Nonidet™ P-40 nonionic surfactant (0.45 % by weight) and Tween™ 20 nonionic surfactant (0.45 % by weight) were mixed in solution. This solution was autoclaved, and stored in frozen form. Before use, it was thawed, and a solution of proteinase K (10 mg/ml) was added (0.6 µl of enzyme solution per 100 µl of the thawed solution).

The lysing composition useful in this invention was prepared exactly like the Control composition except no proteinase K was added before its use.

The PCR solution used in the amplification contained: tris(hydroxymethyl)aminomethane hydrochloride buffer (100 mmolar, pH 8), gelatin ( 1 µg/ml), potassium chloride (500 mmolar), magnesium chloride (100 mmolar), dNTP's (6 µl containing 1.5 mmolar of each dNTP), DNA polymerase derived from Thermus aquaticus (7.5 Units, 4 Units/ml) and the primers noted above (10 µmolar of each).

EXAMPLE 1

Extraction of HIV-I DNA from Patient Whole Blood Samples

This example demonstrates the practice of the extraction method of this invention and compares it to the prior art method using the lysis composition of U.S. patent application Ser. No. 178,202 (noted above).

The following procedure was used to test several different whole blood samples obtained from HIV-I infected patients at a local hospital. Each sample (8 ml) was collected in Leucoprep™ tubes, centrifuged at 18,000×g for 20 minutes at room temperature, and the resulting plasma and cell layers (about 6 ml) were carefully removed and transferred to 15 ml conical tubes. An equal volume of Hanks balanced salt solution was added, and the conical tube was inverted several times to mix the solution. It was then centrifuged at 300×g for 10 minutes at room temperature, and the supernatant was removed and discarded. The pellet was resuspended in Hanks balanced salt solution (3 ml) and vortexed to obtain complete cell suspension. The cells were then counted, and the solution was divided into two volumes (about 1.5 ml each). The two solutions were centrifuged at 14,000 rpm for 10 minutes, and each supernatant removed and discarded. The resulting cell pellets were frozen at −20° C. for later DNA extraction or evaluated immediately. One cell pellet was extracted using the method of this invention and the other using the Control method (using proteinase K lysing composition).

The method of this invention was carried out as follows:

A cell pellet obtained as described above was added to the lysing composition lacking proteinase K (50 µl) and vortexed to break up the pellet. The resulting solution was then heated at 100° C. for 10 minutes and centrifuged for about 2 seconds at 14,000 rpm. The DNA obtained thereby was quantitated, and about 1 µg of DNA per reaction tube was amplified using polymerase chain reaction as described below.

The second cell pellet of each patient sample described above was added to the Control composition (50 µl) and vortexed to break up the pellet. The resulting solution was incubated at 50°–60° C. for one hour, then incubated at 95° C. for 10 minutes. After centrifugation at 14,000 rpm for about 2 seconds, the DNA was quantitated. About 1 μg of DNA per reaction tube was amplified using polymerase chain reaction as described below.

It is to be observed that the Control extraction procedure required over 1 hour, and two different heating steps at different temperatures. The procedure of the present invention was simpler in that only one heating step was needed, and it required only about twelve minutes including ten minutes of heating. These advantages are particularly important where extraction and amplification is to be carried out in clinical laboratories and doctors' offices were many patient samples will be tested in a limited time period with limited personnel. Thus, the extraction method of this invention is more practical for high volume testing.

EXAMPLE 2

Amplification of Extracted HIV-I DNA

This example demonstrates amplification of the DNA extracted in Example 1 using polymerase chain reaction.

Samples (1 μg each) of DNA extracted in Example 1 from the present invention as well as the Control extraction method were amplified using polymerase chain reaction in the following manner. The DNA samples (in 25 μl) were mixed with PCR solution (identified above, 200 μl) and amplified for 32 cycles, each cycle comprising: heating to 97° C. over a one minute period, holding at 97° C. for 30 seconds, cooling to 55° C. over 1.5 minutes, holding at 55° C. for 30 seconds, heating to 70° C. over a 45 second period, and holding at 70° C. for 1 minute. Aliquots (6 μl) were then withdrawn and applied to 4% agarose gels which had been prestained with ethidium bromide (4 μl of 10 mg/ml of water). The running buffer contained ethidium bromide solution (24 μl). The gel was electrophoresed at 120 volts for 1 hour, then photographed, and the bands were visualized.

The present invention, in every replicate, was much more rapid and simpler than the prior art Control method of U.S. patent application Ser. No. 178,202 (noted above). In some cases, the ethidium bromide bands of the present invention were more intense than the bands obtained with the Control method, but this comparison was not seen in every replicate.

The invention has been described in detail with particular reference to preferred embodiments thereof, but it will be understood that variations and modifications can be effected within the spirit and scope of the invention.

We claim:

1. A method for the rapid extraction of a targeted deoxyribonucleic acid from cells or virions, said method consisting essentially of:
   (A) mixing an animal or human sample of whole blood or a component thereof containing cells or virions containing one or more deoxyribonucleic acids with a lysing composition to extract said deoxyribonucleoic acids from said cells or virions, said lysing composition comprising,
      (1) an organic buffer which maintains said composition at a pH of from about 4 to about 10,
      (2) a catalytic amount of a free metal ion cofactor for DNA polymerase activity,
      (3) a stabilizing material which is water-soluble or water-dispersible high molecular weight binder material selected from the group consisting of gelatin, a gelatin derivative, cellulose, a cellulose derivative, polyvinyl alcohol, and polyethylene glycol,
      (4) at least one compatible nonionic surfactant present in an amount sufficient to release said deoxyribonucleic acids from said cells or virions,
   provided a proteolytic enzyme is not deliberately added to said lysing composition,
   (B) heating the resulting mixture at from 80° to 120° C. for from about five to about fifteen minutes, and
   (C) recovering said nucleic acids from said heated mixture.

2. The method of claim 1 wherein said composition further comprises a salt in an amount of from about 1 to about 150 mmolar.

3. The method of claim 1 wherein said composition pH is maintained at a pH of from about 7 to about 9.

4. The method of claim 1 wherein said DNA polymerase cofactor is supplied as a magnesium or manganese salt.

5. A method for the rapid extraction of a targeted deoxyribonucleic acid from cells or virions, said method consisting essentially of:
   A. mixing an animal or human sample of whole blood or a component thereof containing cells or virions containing one or more deoxyribonucleic acids with a lysing composition to extract said deoxyribonucleotide acids from said cells or virions, said lysing composition comprising,
      (1) an organic buffer which maintains said composition at a pH of from about 4 to about 10,
      (2) a catalytic amount of a free metal ion cofactor for DNA polymerase activity,
      (3) gelatin or a derivative thereof
      (4) at least one compatible nonionic surfactant present in an amount sufficient to release said deoxyribonucleic acids from said cells or virions.
   provided a proteolytic enzyme is not deliberately added to said lysing composition,
   (B) heating the resulting mixture at from 80° to 120° C. for from about five to about fifteen minutes, and
   (C) recovering said nucleic acids from said heated mixture.

6. The method of claim 1 wherein said composition comprises two nonionic surfactants, one being a polyoxyethylenesorbitan derivative and the second being a polyoxyethylene ether.

7. The method of claim 1 wherein said nonionic surfactant is present in an amount of from about 0.1 to about 5 percent, based on total composition weight.

8. The method of claim 1 wherein said mixture is heated for from about eight to about twelve minutes.

9. The method of claim 1 for the extraction of vital DNA.

10. A method for the rapid extraction of HIV-I DNA from a patient specimen, said method consisting essentially of:
   (A) mixing a patient specimen believed to contain HIV-I infected cells with a lysing composition comprising,
      (1) an organic buffer which maintains said composition at a pH of from about 4 to about 10,
      (2) a source of at least about 0.5 mmolar of magnesium ion,
      (3) a stabilizing material which is water-soluble or water-dispersible high molecular weight binder material selected from the group consisting of gelatin, a gelatin derivative, cellulose, a cellulose derivative, polyvinyl alcohol, and polyethylene glycol,
      (4) at least one compatible nonionic surfactant present in an amount sufficient to release HIV-I DNA from cytoplasmic and nuclear membranes of said cells, provided a proteolytic enzyme is not deliberately added to said lysing composition, (B) heating the resulting mixture at from 80° to 120+ C. for from about five to about fifteen minutes, and (C) recovering HIV-I DNA from said heated mixture.

11. The method of claim 10 wherein said patient sample is whole blood or a component thereof.

12. The method of claim 10 wherein said composition comprises two nonionic surfactants, one being a polyoxyethylenesorbitan derivative and the second being a polyoxyethylene ether.

13. The method of claim 10 wherein said nonionic surfactant is present in an amount of from about 0.5 to about 5 percent, based on total composition weight.

14. The method of claim 10 wherein said mixture is heated for from about eight to about twelve minutes.

15. A method for the rapid extraction of a targeted deoxyribonucleic acid from cells or virions, said method consisting essentially of:

(A) mixing a human or animal sample of whole blood or a component thereof containing cells or virions containing one or more targeted deoxyribonucleic acids with a lysing composition comprising, (1) tris(hydroxymethyl)aminomethane to maintain said composition at a pH of from about 7 to about 9, (2) from about 1 to about 150 molar potassium chloride, (3) from about 0.5 to about 20 molar magnesium ion, (4) from about 0.1 to about 10 mg of gelatin per ml of composition, (5) from about 0.1 to about 5 percent of a polyoxyethylenesorbitan derivative nonionic surfactant, based on total composition weight, (6) from about 0.1 to about 5 percent of a polyoxyethylene ether nonionic surfactant, based on a total composition weight, provided a proteolytic enzyme is not deliberately added to said lysing composition, B. heating the resulting mixture at or near the boiling water for from about eight to about twelve minutes.

* * * * *